US00PP12435P2

(12) United States Plant Patent
Meier et al.

(10) Patent No.: US PP12,435 P2
(45) **Date of Patent: *Mar. 5, 2002**

(54) KENTUCKY BLUEGRASS DESIGNATED 'BA81-227'

(75) Inventors: Virgil D. Meier, Marysville, OH (US); Jay B. Burr, Salem, OR (US)

(73) Assignee: OMS Investments, Inc., Wilmington, DE (US)

( * ) Notice: Subject to any disclaimer, the term of this patent is extended or adjusted under 35 U.S.C. 154(b) by 16 days.

(21) Appl. No.: 09/709,110

(22) Filed: Nov. 10, 2000

(51) Int. Cl.[7] ..... A01H 5/00
(52) U.S. Cl. ..... Plt./393
(58) Field of Search ..... Plt./393

(56) References Cited

U.S. PATENT DOCUMENTS

| | | | | |
|---|---|---|---|---|
| PP3,150 | P | 5/1972 | Pepin et al. | Plt./393 |
| PP3,156 | P | 5/1972 | Fuchigami et al. | Plt./393 |
| PP3,186 | P | 5/1972 | Barenbrug et al. | Plt./393 |
| PP4,336 | P | 11/1978 | Mayer et al. | Plt./393 |
| PP6,280 | P | 9/1988 | Meier et al. | Plt./393 |
| PP6,537 | P | 1/1989 | Meier et al. | Plt./393 |
| PP6,538 | P | 1/1989 | Meier et al. | Plt./393 |
| PP6,585 | P | 2/1989 | Meier et al. | Plt./393 |
| PP7,831 | P | 3/1992 | Meier et al. | Plt./393 |
| PP8,490 | P | 12/1993 | Meier et al. | Plt./393 |
| PP9,036 | P | 1/1995 | Meier et al. | Plt./393 |
| PP9,209 | P | 7/1995 | Meier et al. | Plt./393 |
| PP9,611 | P | 7/1996 | Meier | Plt./393 |
| PP9,848 | P | 4/1997 | Meier et al. | Plt./393 |
| PP9,977 | P | 7/1997 | Meier et al. | Plt./393 |
| PP10,080 | P | 10/1997 | Meier et al. | Plt./393 |
| PP10,081 | P | 10/1997 | Meier et al. | Plt./393 |
| PP10,384 | P | 5/1998 | Meier et al. | Plt./393 |
| PP10,925 | P | 5/1999 | Meier et al. | Plt./393 |
| PP11,520 | P | 9/2000 | Meier et al. | Plt./393 |
| PP11,536 | P | 10/2000 | Meier et al. | Plt./393 |

*Primary Examiner*—Bruce R. Campell
*Assistant Examiner*—Annette H. Para
(74) *Attorney, Agent, or Firm*—Jones, Day, Reavis & Pogue

(57) ABSTRACT

A variety of Kentucky bluegrass having a medium to high level of resistance to melting out, leaf spot, summer patch, stem rust and crown rust, a medium green color throughout the growing season; good fall color, good winter color during mild winters; the ability to form a good quality turf under a wide variety of environmental conditions providing good sod strength and good tolerance to wear; and a medium to high level of seed yielding capacity.

3 Drawing Sheets

BACKGROUND OF THE INVENTION

1. Field of the Invention

The present invention relates to a new and distinct variety of *Poa pratensis* that has been designated 'Ba81-227' Kentucky bluegrass.

2. Description of Related Art

Kentucky Bluegrasses have been disclosed in U.S. Plant Pat. No. 3,150, issued May 2, 1972; U.S. Plant Pat. No. 3,156, issued May 9, 1972; U.S. Plant Pat. No. 3,186, issued May 23, 1972; U.S. Plant Pat. No. 4,336, issued Nov. 28, 1978; U.S. Plant Pat. No. 6,280, issued Sep. 6, 1988; U.S. Plant Pat. No. 6,537 and 6,538, issued on Jan. 17, 1989; U.S. Plant Pat. No. 6,585, issued Feb. 7, 1989; U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995; U.S. Plant Pat. No. 9,290, issued Jul. 18, 1995; U.S. Plant Pat. No. 9,611, issued Jul. 23, 1996; U.S. Plant Pat. No. 9,848, issued Apr. 1, 1997; U.S. Plant Pat. No. 9,977, issued Jul. 22, 1997; U.S. Plant Pat. No. 10,080, issued Oct. 21, 1997; U.S. Plant Pat. No. 10,081, issued Oct. 21, 1997; U.S. Plant Pat. No. 10,384, issued May 5, 1998; U.S. Plant Pat. No. 10,925, issued May 25, 1999; U.S. Plant Pat. No. 11,520, issued Sep. 26, 2000; U.S. Plant Pat. No. 11,536, issued Oct. 3, 2000; and pending U.S. Plant patent application Ser. No. 09/120,718, filed Jul. 22, 1998, as well as U.S. Plant patent application Ser. No. 09/578,128, filed May 24, 2000.

SUMMARY OF THE VARIETY

'Ba81-227' plant material originated from a single plant that was a progeny resulting from crossing 'Ba79-127' Kentucky bluegrass, as the seed parent, with 'Ba79-129' Kentucky bluegrass, as the pollen parent.

'Ba79-127' Kentucky bluegrass is an unreleased, unpatented Kentucky bluegrass plant grown and maintained in the plant nursery at the Scotts Company in Marysville, Ohio and was derived from a plant selected from 'Newport' Kentucky bluegrass. 'Ba79-129' Kentucky bluegrass is an unreleased, unpatented Kentucky blue grass plant grown and maintained in the plant nursery at the Scotts Company in Marysville, Ohio and was derived from a plant selected from 'Vantage' Kentucky bluegrass.

As a result of this breeding, a distinct variety was produced and asexually propagated by rhizomes, tillers and disseminules. The highly apomictic seed of 'Ba81-227' Kentucky bluegrass was produced first at Marysville, Ohio, and later at Gervais, Oreg. This seed was used to plant turf performance evaluation trials and later, seed production fields.

The seed of 'Ba81-227' has been found to be stable. Asexual production of 'Ba81-227' initially was performed at Marysville, Ohio by propagules (tillers and rhizomes) and by disseminules (modified caryopses produced by apomixis), and has consistently produced progeny plants indistinguishable from the first generation asexual reproductions of the instant plant. The apomixis level of 'Ba81-227' is approximately 94.0% (plus or minus 3.7%). The apoximis level was determined by examining seedling characteristics of approximately 75 to 150 seedlings from seven different crop years in a growth chamber and any seedling with one or more characteristics different from 'Ba81-227' seedlings was classified as not being of apomictic origin.

'Ba81-227' has a number of highly desirable characteristics, including a medium to high level of resistance to *Drechslera poae* that causes melting out and leaf spot; a medium to high level of resistance to *Magnaporthe poae* that causes summer patch; a medium to high level of resistance to *Ustilago striiformis* that causes stripe smut, a medium level of resistance to *Erysiphe graminis* that causes powdery mildew, a medium to high level of resistance to *Puccinia graminis* that causes stem rust, and a medium to high level of resistance to *Puccinia coronata* that causes crown rust. 'Ba81-227' has an attractive leafy turf type, and a medium green color which can be maintained throughout the entire growing season. 'Ba81-227' provides good sod strength and good tolerance to wear. 'Ba81-227' demonstrates good fall color and good winter color under mild winter conditions.

'Ba81-227' is an overall good turfgrass performer as evidenced by good scores for quality and color throughout the cool season in turfgrass growing regions of the United States. 'Ba81-227' has a medium to high seed yield potential in the bluegrass seed production region of the northwestern United States.

In comparison with other Kentucky bluegrass varieties, 'Ba81-227' has a larger seed (longer and wider) with a lower number of seeds per pound. The vegetative leaves of unmowed mature plants of 'Ba81-227' Kentucky bluegrass are thicker with longer ligules and with fewer hairs on the upper margin of the ligule, collar margin and dorsal side of the leaf sheath than other Kentucky bluegrasses. The culm is longer with a longer top internode than other Kentucky bluegrass varieties.

DETAILED DESCRIPTION OF THE VARIETY

Figure 1:
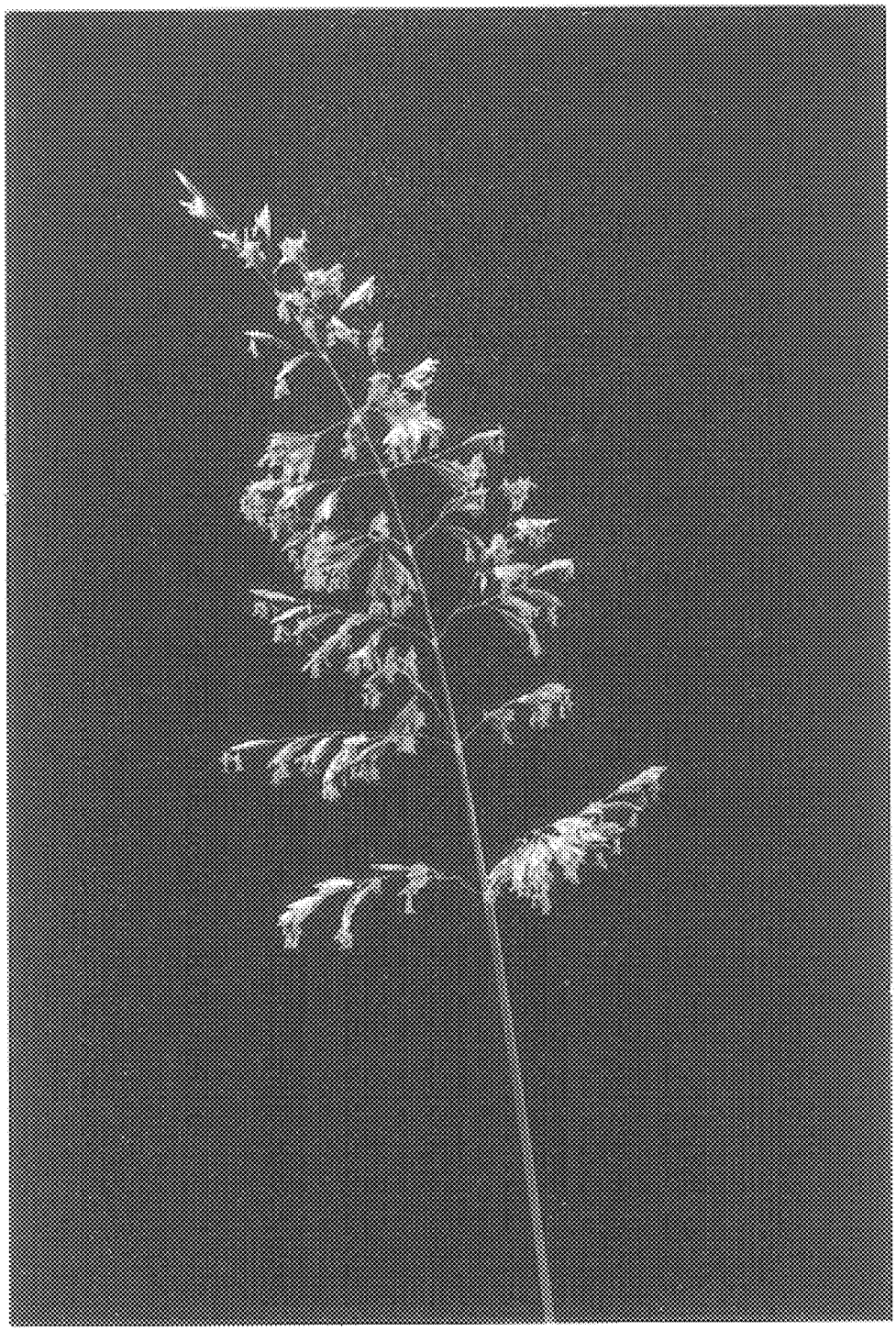
FIG. 1 is a 'Ba81-227' Kentucky bluegrass panicle.
Figure 2:
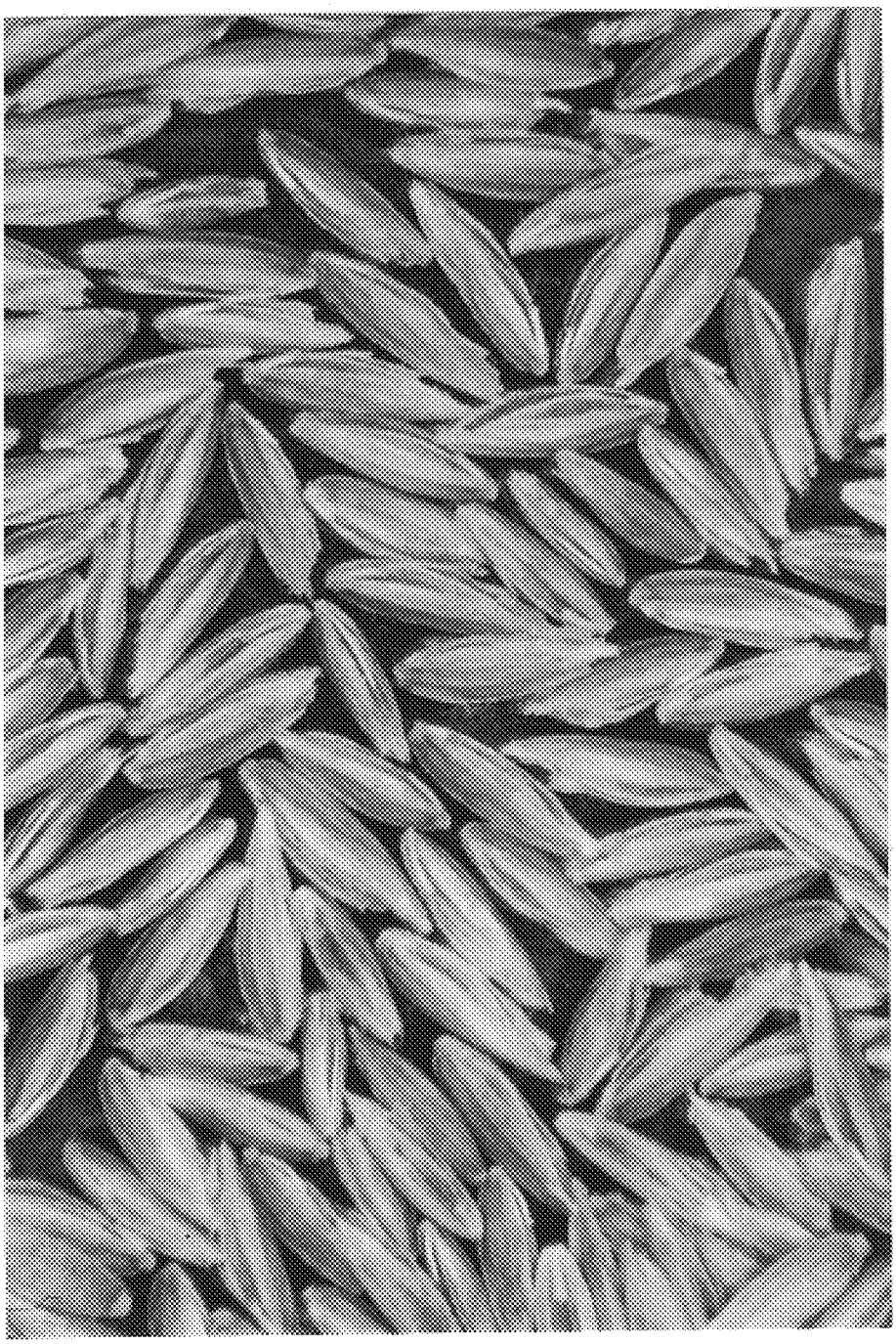
FIG. 2 is a 'Ba81-227' Kentucky bluegrass seed.
Figure 3:
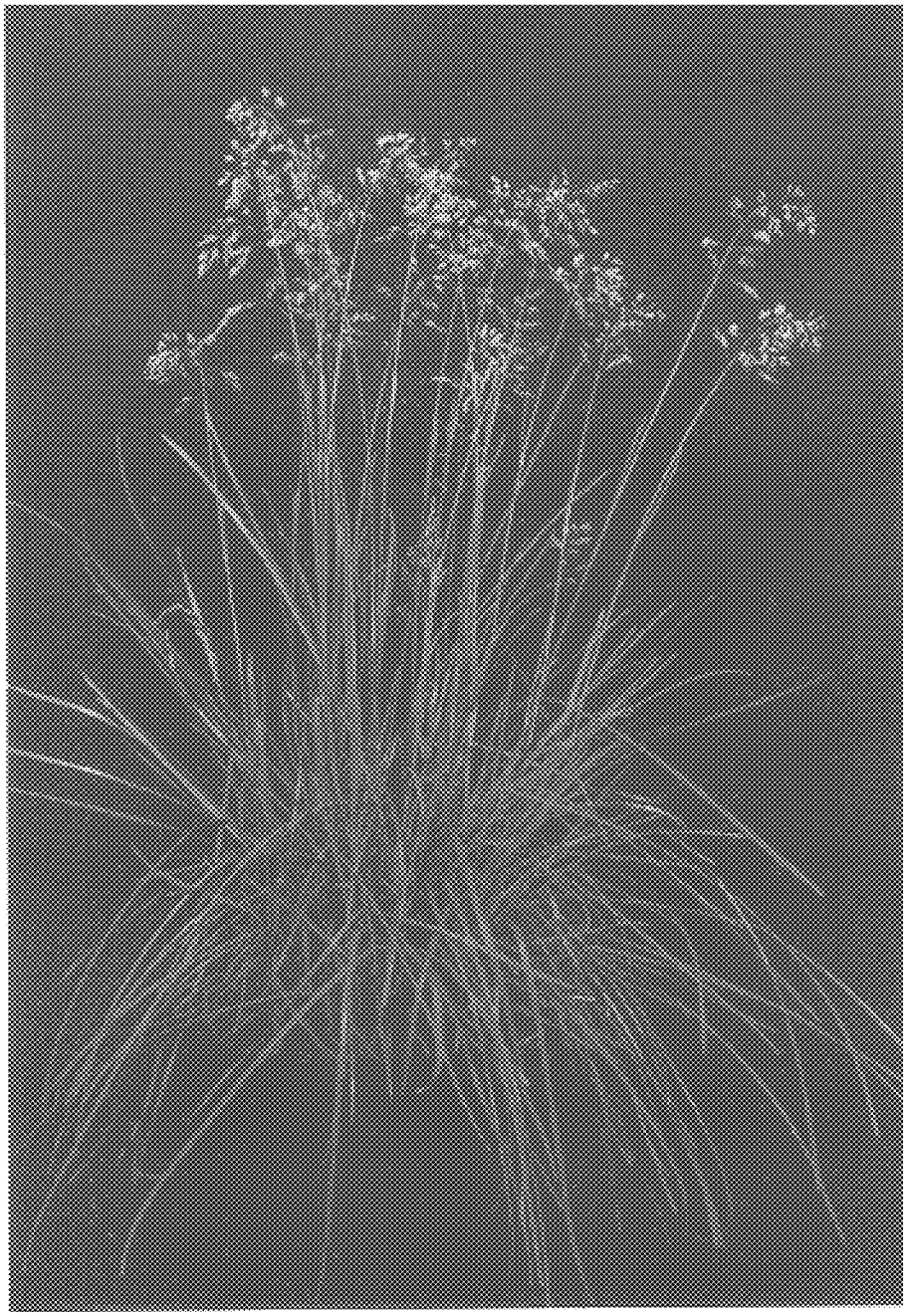
FIG. 3 is a 'Ba81-227' Kentucky bluegrass plant shortly after completing anthesis.

'Ba81-227' Kentucky bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60–80° F.), culms are erect averging 49.3 cm in length. The uppermost internode averages 10.23 cm in length. The peduncle averages 23.3 cm in length and 0.80 mm in width. The vegetative leaf averages 30.5 cm in length, 3.8 mm in width, 0.36 mm in thickness and the ligule 0.40 mm in length. The flag leaf averages 5.6 cm in length, 3.2 mm in width, 0.10 mm in thickness and a ligule length of 0.95 mm. The flag leaf averages fewer hairs on the ligule than other varieties.

The panicle averages 7.8 cm in length, 5.3 cm in width, and has 6.4 whorls. The lowest whorl and the third whorl from the bottom of the panicle both average 2.5 branches, respectively. A spikelet in the lowest whorl averages 4.6 mm in length, 2.1 mm in width, 1.9 florets and the outer glume and inner glume average 2.6 mm and 3.3 mm in length, respectively. A spikelet from the third whorl from the bottom of the panicle averages 4.5 mm in length, 2.8 mm in width, 3.1 florets, and the outer glume and inner glume averages 3.3 mm and 3.7 mm in length, respectively.

For the vegetative leaf, the number of hairs is below average for the leaf sheath margin, below average for the dorsal side of the leaf sheath, below average for the upper margin of the ligule, and below average for the collar margin compared to other varieties. 'Ba81-227' differs from the other Kentucky bluegrass varieties in regard to such morphological characteristics as seed length and width, culm length, top internode length, number of nodes in the culm, vegetative leaf ligule length, and hairs on the upper margin of the vegetative leaf ligule, on the collar margins of the vegetative leaf, on the dorsal side of the vegetative leaf sheath, on the upper surface of the vegetative leaf, and on the ligule of the flag leaf.

Since environmental conditions such as soil and climate may influence morphological characteristics to some extent, comparisons of 'Ba81-227' were made with other Kentucky bluegrass varieties under like conditions and the comparisons are set forth in Tables 1–7, as follows.

TABLE 1

Morphological Comparisons of Peduncles, Culms, Nodes, and Top Internodes of 'Ba81-227' with Other Kentucky Bluegrass Varieties in the Greenhouse at Marysville, Ohio.

| Variety | Peduncle Length (cm) | Peduncle Width (mm) | Culm Length (cm) | Number of Nodes | Top Internode Length (cm) |
|---|---|---|---|---|---|
| 'Ba81-227' | 23.32 | 0.80 | 49.3 | 2.1 | 10.23 |
| 'Abbey' | 23.20 | 0.87 | 45.1 | 3.0 | 7.44 |
| 'Ascot' | 21.17 | 0.73 | 40.6 | 2.2 | 6.54 |
| 'Coventry' | 22.54 | 0.79 | 42.8 | 2.6 | 8.22 |
| 'Envicta' | 20.78 | 0.90 | 45.7 | 2.9 | 7.57 |
| LSD (.05) | 2.39 | 0.09 | 2.8 | 0.4 | 1.56 |

TABLE 2

Morphological Comparisons of Vegetative Leaves of 'Ba81-227' and Other Kentucky Bluegrass Varieties in the Greenhouse at Marysville, Ohio.

| Variety | Length (cm) | Width (mm) | Thickness (mm) | Ligule Length (mm) |
|---|---|---|---|---|
| 'Ba81-227' | 30.46 | 3.80 | 0.359 | 0.40 |
| 'Abbey' | 29.39 | 3.70 | 0.303 | 0.33 |
| 'Ascot' | 25.19 | 3.61 | 0.288 | 0.29 |
| 'Coventry' | 29.92 | 3.18 | 0.267 | 0.24 |
| 'Envicta' | 26.94 | 3.71 | 0.276 | 0.34 |
| LSD (.05) | 3.69 | 0.37 | 0.037 | 0.04 |

TABLE 3

Morphological Comparisons of Flag Leaves of 'Ba81-227' and Other Kentucky Bluegrass Varieties in the Greenhouse at Marysville, Ohio.

| Variety | Length (cm) | Width (mm) | Thickness (mm) | Ligule Length (mm) | Ligule Hair* |
|---|---|---|---|---|---|
| 'Ba81-227' | 5.60 | 3.23 | 0.191 | 0.95 | 1.8 |
| 'Abbey' | 5.47 | 3.48 | 0.246 | 1.06 | 3.3 |
| 'Ascot' | 3.09 | 2.62 | 0.233 | 0.90 | 3.2 |
| 'Coventry' | 4.86 | 3.23 | 0.247 | 0.97 | 3.7 |
| 'Envicta' | 6.05 | 3.80 | 0.265 | 1.13 | 6.1 |
| LSD (.05) | 0.97 | 0.36 | 0.037 | 0.0153 | 1.2 |

*Rating 0–9; 0 = none; 9 = many hairs.

TABLE 4

Morphological Comparisons for Panicle Length and Width, Whorl Number and Whorl Branches of 'Ba81-227' and Other Kentucky Bluegrass Varieties Grown in the Greenhouse at Marysville, Ohio.

| | Panicle | | | Number of Branches | |
|---|---|---|---|---|---|
| Variety | Length (cm) | Width (cm) | Whorl No. | Lowest Whorl | Third Whorl |
| 'Ba81-227' | 7.80 | 5.35 | 6.4 | 2.5 | 2.5 |
| 'Abbey' | 8.29 | 6.62 | 5.9 | 3.6 | 3.3 |
| 'Ascot' | 7.14 | 5.92 | 5.4 | 2.4 | 2.2 |
| 'Coventry' | 7.00 | 6.05 | 5.4 | 3.2 | 3.2 |
| 'Envicta' | 8.24 | 7.30 | 5.8 | 4.4 | 3.5 |
| LSD (0.5) | 0.73 | 0.94 | 0.6 | 0.7 | 0.5 |

TABLE 5

Morphological Comparisons of Spikelets and Florets of 'Ba81-227' and Other Kentucky Bluegrass Varieties in the Greenhouse at Marysville, Ohio.

| | Spikelets | | | | No. of | |
|---|---|---|---|---|---|---|
| | Lowest Whorl | | Third Whorl | | Florets per Spikelet | |
| Variety | Length (mm) | Width (mm) | Length (mm) | Width (mm) | Lowest Whorl | Third Whorl |
| 'Ba81-227' | 4.62 | 2.08 | 4.54 | 2.81 | 1.9 | 3.1 |
| 'Abbey' | 4.50 | 1.88 | 4.78 | 2.04 | 2.0 | 3.4 |
| 'Ascot' | 4.45 | 1.67 | 4.58 | 1.97 | 1.7 | 2.7 |
| 'Coventry' | 4.70 | 1.93 | 4.69 | 1.77 | 3.2 | 3.5 |
| 'Envicta' | 4.38 | 1.96 | 4.55 | 2.01 | 2.7 | 3.1 |
| LSD (.05) | 0.52 | 0.30 | 0.49 | 0.38 | 0.6 | 0.6 |

TABLE 6

Morphpological Comparisons of Glume Size of 'Ba81-227' and Other Kentucky Bluegrass Varieties in the Greenhouse at Marysville, Ohio.

| | Outer Glume Length (mm) | | Inner Glume Length (mm) | |
|---|---|---|---|---|
| Variety | Lowest Whorl | Third Whorl | Lowest Whorl | Third Whorl |
| 'Ba81-227' | 2.63 | 3.32 | 3.29 | 3.68 |
| 'Abbey' | 2.69 | 2.82 | 3.04 | 3.36 |
| 'Ascot' | 3.32 | 3.54 | 3.70 | 3.66 |
| 'Coventry' | 2.71 | 2.92 | 3.20 | 3.23 |
| 'Envicta' | 2.82 | 2.79 | 3.20 | 3.30 |
| LSD (.05) | 0.34 | 0.28 | 0.30 | 0.25 |

TABLE 7

Morphological Comparisons of the Level of Hairs on the Vegetative Leaves of 'Ba81-227' and Other Kentucky Bluegrass Varieties in the Greenhouse at Marysville, Ohio.*

| Variety | Leaf Sheath Margin | Ligule Upper Margin | Collar Margin | Leaf Sheath Dorsal | Leaf Blade Upper Side |
|---|---|---|---|---|---|
| 'Ba81-227' | 0.0 | 1.0 | 0.9 | 0.0 | 1.6 |
| 'Abbey' | 0.1 | 3.0 | 3.0 | 2.1 | 0.0 |
| 'Ascot' | 0.7 | 2.6 | 4.8 | 0.8 | 0.0 |
| 'Coventry' | 1.2 | 3.5 | 3.6 | 1.4 | 0.0 |
| 'Envicta' | 0.5 | 3.3 | 3.3 | 1.4 | 0.0 |
| LSD (.05) | 0.6 | 0.5 | 0.7 | 0.7 | 0.3 |

*Rating scale: 0–9; 0 = None; 9 = many Hairs.

The seed of 'Ba81-227' was conditioned by removing most of the extraneous materials that may have been harvested with the seed, such as small pieces of plant stems and leaves, soil particles, seed of other plants, hair attached to the seed and the like. This conditioned seed of 'Ba81-227' averages 3.37 mm in length, and 0.96 mm in width. 'Ba81-227' has about 871,200 seeds per pound.

Comparisons of 'Ba81-227' with other Kentucky bluegrass varieties in terms of seed numbers per pound and other seed characteristics are shown in Tables 8–9 as follows:

TABLE 8

Morphological Comparisons of Conditional Seed of 'Ba81-227' and Other Kentucky Bluegrass Varieties.

| Variety | Length (mm) | Width (mm) |
|---|---|---|
| 'Ba81-227' | 3.37 | 0.96 |
| 'Abbey' | 2.99 | 0.84 |
| 'Ascot' | 3.19 | 0.82 |
| 'Conventry' | 2.62 | 0.77 |
| 'Envicta' | 3.20 | 0.88 |
| LSD (.05) | 0.16 | 0.06 |

TABLE 9

Comparison of Seeds Per Pound of 'Ba81-227' and Other Kentucky Bluegrass Varieties After Conditioning.

| Variety | Seeds per Pound |
|---|---|
| 'Ba81-227' | 817,200 |
| 'Abbey' | 1,003,000 |
| 'Ascot' | 1,039,400 |
| 'Conventry' | 1,374,700 |
| 'Envicta' | 860,930 |
| 'Famous' | 1,127,500 |
| 'Goldrush' | 942,700 |
| 'Misty' | 1,126,400 |
| 'Nottingham' | 1,071,300 |
| 'Raven' | 1,001,400 |
| 'Sidekick' | 987,300 |
| LSD (.05) | 38,080 |

'Ba81-227' has performed well throughout the U.S. as exhibited by good turf quality ratings in both the sun and shade in comparison with other Kentucky bluegrass varieties. In addition, it has a medium green color with good turf density which can be maintained throughout the growing season providing good sod strength and good tolerance to wear, and a medium to high seed yielding capacity.

With regard to a comparative analysis conducted for purposes of determining color of 'Ba81-227' plants relative to other Kentucky bluegrass varieties, readings were taken of the vegetative color of 'Ba81-227' during mid-October while the turf was actively growing with adequate nutrient and water availability. The readings were taken in full sun with several actively growing leaves being compared, one at a time, utilizing color chips from the Munsell Book of Color as a reference. On this basis, the color of 'Ba81-227' was determined to be 5 GY ¾. During the same time period, the color of similar leaves of other Kentucky bluegrass varieties were determined by the same procedure to be as follows: 'Ascot'—5 GY 4/4; Buckingham—7.5 GY 4/4; 'Envicta'—5 GY 4/4, 'Nottingham'—5 GY 4/6; 'Midnight'—7.5 GY 4/4; 'Abbey'—5 GY 4/6; and 'Victa'—5 GY 4/4. However, it should be noted that the general apparent color of turf does not always correlate directly with the color of the individual actively growing leaves within the turf and that turf color varies with nutrient level and time of year with some varieties being darker or lighter green, depending on such factors.

Comparisons of 'Ba81-227' with other Kentucky bluegrass varieties for quality, genetic color, fall color, winter color, turf density, leaf texture, wear tolerance, sod strength and spread (lateral growth while being mowed), and seed yield are set forth hereinafter in Tables 10–17 as follows.

TABLE 10

A Comparison of Quality of 'Ba81-227' and Other Kentucky Bluegrass Varieties as Affected by Environmental Conditions.

| | Shade[1] | Sun[2] |
|---|---|---|
| 'Ba81-227' | 4.9 | 5.6 |
| 'Abbey' | 4.2 | 5.4 |
| 'Allure' | 5.4 | 5.5 |
| 'America' | 5.3 | 6.1 |
| 'Ascot' | 5.4 | 5.4 |
| 'Baron' | 3.7 | 5.2 |
| 'Blacksburg' | 3.6 | 6.0 |
| 'Challenger' | 4.5 | 5.4 |
| 'Classic' | 4.7 | 5.5 |
| 'Coventry' | 5.1 | 5.5 |
| 'Eclipse' | 4.6 | 5.9 |
| 'Envicta' | 5.1 | 5.4 |
| 'Glade' | 4.4 | 5.9 |
| 'Goldrush' | 4.7 | 5.3 |
| 'Haga' | 5.0 | 5.5 |
| 'Kenblue' | 3.2 | 4.8 |
| 'Limousine' | 4.8 | 5.5 |
| 'Midnight' | 3.2 | 6.4 |
| 'Misty' | 4.4 | 5.4 |
| 'Raven' | 3.4 | 5.5 |
| 'Sebring' | 4.7 | 5.5 |
| 'Sidekick' | 4.3 | 5.3 |
| 'Unique' | 5.3 | 6.1 |
| LSD (.05) | 1.6 | 0.2 |

Rating Scale: 0–9; 9 = Excellent.
[1]From Maryland
[2]From 26 different locations in the U.S.

TABLE 11

A Comparison of Quality of 'Ba81-227' and Other Kentucky Bluegrass Varieties as Affected by Climatic Regions in the U.S.

| | Transition Zone[1] | Cool Humid[2] | Cool Arid[3] |
|---|---|---|---|
| 'Ba81-227' | 5.1 | 5.8 | 6.2 |
| 'Abbey' | 5.1 | 5.5 | 6.2 |
| 'Allure' | 5.1 | 5.6 | 6.1 |
| 'America' | 5.8 | 6.2 | 6.1 |
| 'Ascot' | 4.7 | 5.5 | 6.3 |
| 'Baron' | 4.7 | 5.2 | 6.2 |
| 'Blacksburg' | 5.1 | 6.4 | 6.7 |
| 'Challenger' | 4.9 | 5.5 | 6.3 |
| 'Classic' | 5.2 | 5.6 | 6.0 |
| 'Coventry' | 5.0 | 5.7 | 6.0 |
| 'Eclipse' | 5.5 | 6.0 | 6.0 |
| 'Envicta' | 5.1 | 5.3 | 6.1 |
| 'Glade' | 5.2 | 6.1 | 6.5 |
| 'Goldrush' | 4.9 | 5.3 | 6.1 |
| 'Haga' | 5.3 | 5.6 | 5.7 |
| 'Kenblue' | 4.6 | 4.9 | 5.2 |
| 'Limousine' | 4.4 | 5.9 | 5.9 |
| 'Midnight' | 6.3 | 6.4 | 6.6 |
| 'Misty' | 4.6 | 5.7 | 6.1 |
| 'Raven' | 4.9 | 5.6 | 6.1 |
| 'Sebring' | 5.1 | 5.6 | 6.3 |
| 'Sidekick' | 5.3 | 5.3 | 5.6 |

TABLE 11-continued

A Comparison of Quality of 'Ba81-227' and Other Kentucky Bluegrass Varieties as Affected by Climatic Regions in the U.S.

| | Transition Zone[1] | Cool Humid[2] | Cool Arid[3] |
|---|---|---|---|
| 'Unique' | 6.1 | 6.2 | 6.3 |
| LSD (.05) | 0.4 | 0.2 | 0.4 |

Rating Scale: 0–9; 9 = Excellent.
[1]From 8 different locations in the U.S.
[2]From 15 different locations in the U.S.
[3]From 3 different locations in the U.S.

TABLE 12

A Comparison of Genetic Color, Fall Color and Winter Color of 'Ba81-227' and Other Kentucky Bluegrass Varieties

| Variety | Genetic Color[1] | Fall Color[2] | Winter Color[3] |
|---|---|---|---|
| 'Ba81-227' | 6.1 | 4.3 | 4.7 |
| 'Abbey' | 6.4 | 4.7 | 4.6 |
| 'Allure' | 6.2 | 4.0 | 4.3 |
| 'America' | 6.7 | 4.3 | 4.2 |
| 'Ascot' | 6.8 | 4.0 | 4.3 |
| 'Baron' | 6.6 | 4.7 | 3.6 |
| 'Blacksburg' | 7.1 | 5.3 | 4.8 |
| 'Challenger' | 6.7 | 4.7 | 5.1 |
| 'Classic' | 6.1 | 4.3 | 5.8 |
| 'Coventry' | 6.2 | 4.7 | 4.0 |
| 'Eclipse' | 6.4 | 4.3 | 5.2 |
| 'Envicta' | 6.7 | 5.7 | 3.9 |
| 'Glade' | 7.3 | 4.7 | 3.9 |
| 'Goldrush' | 6.5 | 4.3 | 3.6 |
| 'Haga' | 5.9 | 4.7 | 4.9 |
| 'Kenblue' | 5.5 | 3.7 | 4.4 |
| 'Limousine' | 5.7 | 4.0 | 3.6 |
| 'Midnight' | 7.7 | 5.3 | 3.7 |
| 'Misty' | 6.4 | 4.3 | 5.5 |
| 'Raven' | 6.5 | 5.0 | 3.8 |
| 'Sebring' | 7.4 | 4.3 | 3.6 |
| 'Sidekick' | 6.3 | 4.0 | 5.3 |
| 'Unique' | 6.4 | 4.3 | 4.1 |
| LSD (.05) | 0.2 | 1.2 | 0.7 |

Ratings 1–9; 9 = Dark Green.
[1]From 25 different locations in the U.S.
[2]From 1 location in the U.S.
[3]From 4 different locations in the U.S.

TABLE 13

A Comparison of Turf Density of 'Ba81-227' and Other Kentucky Bluegrass Varieties

| | Turf Density | | |
|---|---|---|---|
| Variety | Spring[1] | Summer[2] | Fall[3] |
| 'Ba81-227' | 7.3 | 6.6 | 7.0 |
| 'Abbey' | 6.8 | 6.7 | 6.7 |
| 'Allure' | 7.5 | 6.9 | 7.0 |
| 'America' | 7.0 | 7.0 | 7.3 |
| 'Ascot' | 7.2 | 6.8 | 7.1 |
| 'Baron' | 6.9 | 6.7 | 6.8 |
| 'Blacksburg' | 7.2 | 7.4 | 7.4 |
| 'Challenger' | 7.0 | 6.8 | 6.8 |
| 'Classic' | 7.1 | 6.4 | 6.7 |
| 'Coventry' | 7.4 | 6.8 | 6.8 |
| 'Eclipse' | 7.0 | 6.5 | 7.1 |
| 'Envicta' | 6.9 | 6.8 | 6.9 |
| 'Glade' | 7.1 | 7.2 | 7.1 |
| 'Goldrush' | 7.1 | 6.9 | 6.8 |
| 'Haga' | 7.2 | 6.6 | 6.9 |

TABLE 13-continued

A Comparison of Turf Density of 'Ba81-227' and Other Kentucky Bluegrass Varieties

| Variety | Turf Density Spring[1] | Summer[2] | Fall[3] |
|---|---|---|---|
| 'Kenblue' | 5.9 | 6.3 | 6.5 |
| 'Limousine' | 7.6 | 7.8 | 7.6 |
| 'Midnight' | 7.5 | 7.4 | 7.4 |
| 'Misty' | 7.0 | 6.8 | 7.1 |
| 'Raven' | 7.1 | 6.6 | 6.8 |
| 'Sebring' | 6.7 | 6.8 | 6.8 |
| 'Sidekick' | 6.8 | 6.4 | 6.5 |
| 'Unique' | 7.2 | 7.0 | 7.5 |
| LSD (.05) | 0.5 | 0.3 | 0.4 |

Density Rating: 1–9; 9 = maximum density.
[1]From 8 different locations in the U.S.
[2]From 9 different locations in the U.S.
[3]From 12 different locations in the U.S.

TABLE 14

A Comparison of Leaf Texture of 'Ba81-227' and Other Kentucky Bluegrass Varieties

| Variety | Texture[1] |
|---|---|
| 'Ba81-227' | 5.7 |
| 'Abbey' | 5.5 |
| 'Allure' | 5.8 |
| 'America' | 6.7 |
| 'Ascot' | 6.0 |
| 'Baron' | 5.7 |
| 'Blacksburg' | 6.3 |
| 'Challenger' | 6.2 |
| 'Classic' | 6.2 |
| 'Coventry' | 5.6 |
| 'Eclipse' | 6.0 |
| 'Envicta' | 5.5 |
| 'Glade' | 6.5 |
| 'Goldrush' | 6.0 |
| 'Haga' | 6.4 |
| 'Kenblue' | 6.9 |
| 'Limousine' | 7.0 |
| 'Midnight' | 6.4 |
| 'Misty' | 5.2 |
| 'Raven' | 5.6 |
| 'Sebring' | 6.0 |
| 'Sidekick' | 5.1 |
| 'Unique' | 6.8 |
| LSD (.05) | 0.3 |

Texture Rating: 1–9; 9 = fine texture.
[1]From 24 different locations in the U.S.

TABLE 15

A Comparison of Wear Tolerance, Sod Strength, and Spread of 'Ba81-227' and Other Kentucky Bluegrass Varieties

| Variety | Wear Tolerance[1] | Sod Strength[2] | Spread[3] |
|---|---|---|---|
| 'Ba81-227' | 5.3 | 51.7 | 29.1 |
| 'Abbey' | 4.7 | 41.0 | 25.0 |
| 'Allure' | 5.0 | 40.7 | 28.6 |
| 'America' | 6.0 | 51.7 | 27.3 |
| 'Ascot' | 4.3 | 50.0 | 27.0 |
| 'Baron' | 4.3 | 29.7 | 25.6 |
| 'Blacksburg' | 3.3 | 5.0 | 23.6 |
| 'Challenger' | 4.7 | 54.3 | 27.9 |
| 'Classic' | 5.7 | 38.7 | 29.6 |
| 'Coventry' | 6.3 | 50.3 | 27.6 |
| 'Eclipse' | 4.3 | 28.3 | 28.0 |

TABLE 15-continued

A Comparison of Wear Tolerance, Sod Strength, and Spread of 'Ba81-227' and Other Kentucky Bluegrass Varieties

| Variety | Wear Tolerance[1] | Sod Strength[2] | Spread[3] |
|---|---|---|---|
| 'Envicta' | 5.0 | 36.7 | 24.5 |
| 'Glade' | 5.0 | 29.7 | 25.1 |
| 'Goldrush' | 3.7 | 52.0 | 27.9 |
| 'Haga' | 5.3 | 44.3 | 24.8 |
| 'Kenblue' | 6.3 | 35.3 | 25.1 |
| 'Limousine' | 4.7 | 22.0 | 22.9 |
| 'Midnight' | 4.7 | 57.0 | 26.0 |
| 'Misty' | 4.3 | 45.0 | 22.5 |
| 'Raven' | 4.0 | 37.0 | 26.5 |
| 'Sebring' | 5.3 | 21.3 | 22.9 |
| 'Sidekick' | 6.0 | 41.7 | 28.0 |
| 'Unique' | 5.7 | 55.0 | 29.1 |
| LSD (.05) | 1.7 | 29.4 | 4.7 |

[1]From Iowa Rating Scale: 1–9; 9 = Most tolerant to wear.
[2]From Nebraska. Rating Scale: Kilograms of tension needed to tear sod
[3]From Maryland. Rating Scale: Mean diameter (cm) of plants.

TABLE 16

A Comparison of Seed Yield (Pounds per Acre) of 'Ba81-227' and Other Kentucky Bluegrass Varieties at Gervais, Oregon.

| Variety | Seed Yield (lbs/A) |
|---|---|
| 'Ba81-227' | 795 |
| 'Abbey' | 755 |
| 'Coventry' | 569 |
| LSD (.05) | 153 |

TABLE 17

A Comparison of Seed Yield (Pounds per Acre) of 'Ba81-227'and Other Kentucky Bluegrass Varieties at Mesa, Washington.

| Variety | Seed Yield (lbs/A) |
|---|---|
| 'Ba81-227' | 555 |
| 'Abbey' | 684 |
| 'Coventry' | 439 |
| 'Envicta' | 820 |
| LSD (.05) | 237 |

Turf diseases are one of the major causes of inconsistent and poor turf performance. 'Ba81-227' has been found to have a medium to high level of resistance to melting out and leaf spot both of which are caused by *Drechslera poae* (formerly called *Helminthosporium vagans*); a medium to high level of resistance to summer patch caused by *Magnaporthe poae,* a medium to high level of resistance to stripe smut caused by *Ustilago striiformis*, a medium level of resistance to powdery mildew caused by *Erysiphe graminis*, a medium to high level of resistance to stem rust caused by *Puccinia graminis*, and a medium to high level of resistance to crown rust caused by *Puccinia coronata.*

Comparisons of disease incidence of 'Ba81-227' as compared with other Kentucky bluegrass varieties in regard to melting out, leaf spot, summer patch, stripe smut, powdery mildew, stem rust, and crown rust are presented in Table 18 as follows:

TABLE 18

A Comparison of Diseases of 'Ba81-227' and Other Kentucky Bluegrass Varieties.

| Variety | Melting Out[1] | Leaf Spot[2] | Summer Patch[3] | Stripe Smut[4] | Powdery Mildew[5] | Stem Rust[6] | Crown Rust[7] |
|---|---|---|---|---|---|---|---|
| 'Ba81-227' | 8.3 | 6.3 | 8.2 | 8.7 | 5.0 | 8.8 | 9.0 |
| 'Abbey' | 9.0 | 4.0 | 7.0 | 1.7 | 2.3 | 7.3 | 9.0 |
| 'Allure' | 7.0 | 4.3 | 7.7 | 8.0 | 3.3 | 5.7 | 9.0 |
| 'America' | 8.3 | 5.7 | 8.7 | 8.0 | 7.0 | 7.7 | 9.0 |
| 'Ascot' | 8.7 | 8.0 | 5.2 | 6.7 | 5.3 | 5.7 | 8.0 |
| 'Baron' | 9.0 | 3.7 | 6.7 | 1.0 | 2.0 | 7.3 | 9.0 |
| 'Blacksburg' | 6.3 | 7.7 | 7.8 | 6.7 | 4.7 | 7.7 | 8.0 |
| 'Challenger' | 9.0 | 5.7 | 8.2 | 6.0 | 2.7 | 6.7 | 9.0 |
| 'Classic' | 7.0 | 4.3 | 8.5 | 8.3 | 1.0 | 6.0 | 9.0 |
| 'Coventry' | 7.3 | 5.3 | 7.8 | 8.3 | 2.3 | 6.3 | 8.7 |
| 'Eclipse' | 9.0 | 7.7 | 8.7 | 7.7 | 6.3 | 6.7 | 8.7 |
| 'Envicta' | 9.0 | 3.3 | 8.0 | 1.3 | 2.0 | 8.0 | 9.0 |
| 'Glade' | 5.0 | 4.3 | 8.2 | 8.7 | 8.7 | 6.3 | 9.0 |
| 'Goldrush' | 9.0 | 4.3 | 7.0 | 1.7 | 2.0 | 6.3 | 9.0 |
| 'Haga' | 7.7 | 5.3 | 8.3 | 8.3 | 2.3 | 7.0 | 8.7 |
| 'Kenblue' | 1.3 | 1.0 | 6.7 | 9.0 | 6.7 | 3.7 | 8.0 |
| 'Limousine' | 9.0 | 5.7 | 8.5 | 4.7 | 5.3 | 7.0 | 8.7 |
| 'Midnight' | 9.0 | 8.7 | 8.0 | 8.3 | 1.0 | 7.7 | 9.0 |
| 'Misty' | 7.3 | 4.7 | 6.5 | 9.0 | 8.0 | 5.3 | 8.7 |

TABLE 18-continued

A Comparison of Diseases of 'Ba81-227' and Other Kentucky Bluegrass Varieties.

| Variety | Melting Out[1] | Leaf Spot[2] | Summer Patch[3] | Stripe Smut[4] | Powdery Mildew[5] | Stem Rust[6] | Crown Rust[7] |
|---|---|---|---|---|---|---|---|
| 'Raven' | 9.0 | 4.3 | 8.7 | 1.0 | 2.7 | 4.7 | 9.0 |
| 'Sebring' | 9.0 | 7.7 | 9.0 | 7.0 | 4.0 | 5.7 | 9.0 |
| 'Sidekick' | 7.0 | 4.0 | 8.5 | 7.3 | 5.7 | 6.0 | 8.7 |
| 'Unique' | 8.7 | 6.3 | 8.7 | 8.3 | 9.0 | 7.7 | 9.0 |
| LSD (.05) | 1.3 | 1.8 | 1.4 | 1.9 | 1.1 | 3.4 | 1.4 |

Rating Scale: 1–9; 9 = No Disease.
[1]From Pennsylvania
[2]From New Jersey
[3]From 2 different locations in the U.S.
[4]From New Jersey
[5]From New Jersey
[6]From North Carolina
[7]From North Carolina

What is claimed is:

1. A new and distinct variety of Kentucky bluegrass plant, as herein illustrated and described.

* * * * *